United States Patent [19]
Wang et al.

[11] Patent Number: 5,856,085
[45] Date of Patent: Jan. 5, 1999

[54] COMPOSITIONS AND METHODS OF DEVELOPING OLIGONUCLEOTIDES AND OLIGONUCLEOTIDE ANALOGS HAVING ANTIVIRAL ACTIVITY

[75] Inventors: Jin-Feng Wang, Hummelstown; Weihua Pan, Hershey, both of Pa.

[73] Assignee: The Penn State Research Foundation, University Park, Pa.

[21] Appl. No.: 566,216

[22] Filed: Dec. 1, 1995

[51] Int. Cl.$^6$ .................... C12Q 1/70; C12Q 1/68; C12P 19/34; C07H 21/02
[52] U.S. Cl. .................... 435/5; 435/6; 435/91.2; 536/23.1
[58] Field of Search .................... 435/5, 6, 91.1, 435/91.2; 536/23.1

[56] References Cited

U.S. PATENT DOCUMENTS

| | | | |
|---|---|---|---|
| 5,496,938 | 3/1996 | Gold et al. | 536/22.1 |
| 5,503,978 | 4/1996 | Schneider et al. | 435/6 |
| 5,527,894 | 6/1996 | Gold et al. | 536/22.1 |

FOREIGN PATENT DOCUMENTS

WO96/34875  11/1996  WIPO ............ C07H 21/02

OTHER PUBLICATIONS

Pan et al. (Dec. 1995) Proc. Natl. Acad. Sci. USA 92:11509–13.

Johnston et al., "Present Status & Future Prospects for HIV Therapies", Science 260, 1993, pp. 1286–1293.

van der Sijs et al., "Antiviral Drugs: Present Status & Future Prospects", Int. J. Biochem. 26, 1994, pp. 621–630.

Pan et al., "In Vitro Selection of RNAs That Undergo Autolytic Cleavage", Biochemistry 31, 1992, pp. 3887–3895.

Kinzler et al., "Whole Genome PCR: Application to the Identification . . . ", Nucl. Acids Res. 17, 1989, pp. 3645–3653.

Joyce, "Amplification, Mutation & Selection of Catalytic RNA", Gene 82, 1989, pp. 83–87.

Ellington et al., "In Vitro Selection of RNA Molecules That Specific Ligands", Nature 346, 1990, pp. 818–822.

Turek et al., "Systematic Evolution of Ligands by Exponential Enrichment . . . ", Science 249, 1990, pp. 505–510.

Bartel et al., "Isolation of New Ribozymes From a Large Pool of Random Sequences", Science 261, 1993, pp. 1411–1418.

McCune et al., "Suppression of HIV Infection in AZT–Treated SCID–hu Mice", Science 247, 1990, pp. 564–566.

Nielsen et al., "Sequence–Selective Recognition of DNA by Strand Displacement . . . ", Science 254, 1991, pp. 1497–1500.

Cadwell et al., "Randomization of Genes by PCR Mutagenesis", PCR Methods Appl. 2, 1992, pp. 28–33.

*Primary Examiner*—Lisa B. Arthur
*Attorney, Agent, or Firm*—Thomas J. Monahan

[57] ABSTRACT

Methods of identifying and preparing anti-infectious agent compounds comprising the steps of incubating single stranded nucleic acids or nucleic acid analogs in the presence of infectious agents, selecting for nucleic acids or nucleic acid analogs which bind infectious agents, amplifying selected nucleic acids or nucleic acid analogs, repeating the selection steps and assaying for anti-infection activity are disclosed. Compositions that have anti-infectious activity against Rous sarcoma virus are also disclosed. Methods of identifying anti-tumor agent compounds are also disclosed.

34 Claims, 11 Drawing Sheets

```
       5'-fixed              variable 40N                      3'-fixed
5'- gggagcucagaauaaacgcucaa-(40N)-uucgacaugaggcccggauccggc -3'

A:  GGGUAGGGAUCGUUACCCCGACAUUUUAAUGGGCCGAUGU
B:  UGCCCUCGUGUCGAAGAAGGGUGGCGCGAGGUAGGGUUUCGACAUGA
E:  UGUAGUGAACAUUAAUGGAGAGAGGGAGGGUAGGGUUACG
F:  AUUGUCUUGAACCCGUGGAGGGUGUGAGGGUAGGGGUGGUUC
G:  UAAUGUUGGACCUAGUGGAGGGGUGUGGAGGAUUGGUUC
H:  UGUUAGGACCCUCGAGGGAGGUUGCGCAGGGUGGGGAGGG
```

FIGURE 6B

2'-F-pyrimidine-RNA analog

COMPOSITIONS AND METHODS OF DEVELOPING OLIGONUCLEOTIDES AND OLIGONUCLEOTIDE ANALOGS HAVING ANTIVIRAL ACTIVITY

FIELD OF THE INVENTION

The field of the invention is antiviral compositions and methods of generating the same.

BACKGROUND OF THE INVENTION

Although viruses are the causative agents of a number of human and animal diseases, there is currently a paucity of antiviral agents effective in ablating or minimizing virus infection in these hosts. Vaccines have been successfully developed which protect humans against infection by only a few viruses including measles, rubella, mumps, hepatitis A, hepatitis B, influenza and poliomyelitis viruses. However, vaccination has little or no effect in individuals who are infected prior to vaccination. In addition, there are as yet no effective vaccines for the prevention of many viral infections including infection by Human Immunodeficiency Virus (HIV). There is therefore a long felt need for the development of agents for treatment of viral infections in general and in particular, for treatment of those viral infections for which there are no available vaccines.

Traditionally, the most successful approach to the discovery of new antiviral agents has been the empirical screening of large numbers of chemically diverse classes of compounds and natural products for their ability to inhibit virus replication (Johnston et al., 1993, Science 260:1286–1293; van der Sijs et al., 1994, Int. J. Biochem. 26:621–630). Antiviral agents which have been discovered in traditional cell culture screening assays include 3'-azidothymidine (AZT), 2',3'-dideoxyinosine (ddI) and 2',3'-dideoxycytidine (DDC). However, the empirical screening process is usually tedious and inefficient. Additional approaches to the development of antiviral agents such as rational drug design based on the known structures of viral or cellular proteins are promising but have to date had limited success.

The present invention provides a novel and rapid method for screening of compounds for activity in inhibiting infection by infectious agents, which method has significant advantages over conventional screening techniques. Compounds which are generated using the methods of the invention also have significant advantages over currently available anti-infectious agent compositions and in particular antiviral compositions.

SUMMARY OF THE INVENTION

The invention features a method of identifying an anti-infectious agent compound comprising the steps of A) incubating a library of single stranded nucleic acids or nucleic acid analogs in the presence of at least one population of intact infectious agents to effect binding of nucleic acid or nucleic acid analog in the library to the infectious agent, wherein the infectious agent is selected from the group consisting of virus, bacterium, fungus including yeast and parasite; B) separating infectious agent-bound nucleic acid or nucleic acid analog from unbound nucleic acid or nucleic acid analog to obtain a first pool of infectious agent-binding nucleic acid or nucleic acid analog; C) amplifying the first pool of infectious agent-binding nucleic acid or nucleic acid analog; D) incubating the amplified first pool of infectious agent-binding nucleic acid or nucleic acid analog in the presence of at least one population of intact infectious agents to effect binding of the nucleic acid or nucleic acid analog to the infectious agent; E) separating amplified infectious agent-bound nucleic acid or nucleic acid analog from amplified unbound nucleic acid or nucleic acid analog to obtain a second pool of infectious agent-binding nucleic acid or nucleic acid analog; F) repeating amplification step C, incubation step D, and separation step E from zero up to about thirty times sequentially on each subsequently obtained pool of infectious agent-binding nucleic acids or nucleic acid analogs until the binding of the obtained nucleic acids or nucleic acid analogs to the infectious agent does not improve significantly; and G) assaying the obtained infectious agent-binding nucleic acid or nucleic acid analog for the ability to inhibit infection by the infectious agent, wherein inhibition of infection by the infectious agent by the subsequently obtained infectious agent-binding nucleic acid or nucleic acid analog is an indication that the subsequently obtained infectious agent-binding nucleic acid or nucleic acid analog is an anti-infectious agent compound.

By "anti-infectious agent compound" is meant a compound capable of inhibiting infection by an infectious agent.

By "subsequently obtained infectious agent-binding nucleic acid" is meant a nucleic acid which is obtained following each round of binding and amplification. For example, as described above, a second infectious agent-binding nucleic acid is obtained following the second round of binding and amplification. A "subsequently-obtained infectious agent-binding nucleic acid" therefore is a pool of nucleic acid which is obtained following the third or the fourth or the fifth, etc., round of binding and amplification.

The term "amplification" should be construed to include amplification by any means including PCR under conditions designed to faithfully copy the subject sequence and under conditions such that mutations in the subject sequence are introduced at low levels.

By the phrase "until binding of the obtained nucleic acid or nucleic acid analog to the infectious agent does not improve significantly" is meant until binding of the nucleic acid or nucleic acid analog to the infections agent in one cycle is less than about 20% higher than binding of the nucleic acid or nucleic acid analog to the infectious agent in the preceeding cycle.

In one aspect of the method of the invention, the nucleic acid or nucleic acid analog is single stranded RNA or RNA analog. In another aspect, the nucleic acid or nucleic acid analog is single stranded DNA or DNA analog. In a preferred embodiment, the single stranded nucleic acid or nucleic acid analog comprises from about 40 to about 450 nucleotide units.

In yet another aspect of the invention, a core set of nucleotides within the nucleic acid or nucleic acid analog comprises a random nucleotide sequence. Preferably, the core set of nucleotides comprises from about 10 to 350 nucleotide units.

Preferably, the incubation, separation and amplification steps performed sequentially on each subsequently obtained infectious agent-binding nucleic acids or nucleic acid analogs are performed at least two times. More preferably, the incubation and amplification steps performed sequentially on each subsequently obtained infectious agent-binding nucleic acid or nucleic acid analog are performed at least four times. Even more preferably, the incubation, separation and amplification steps performed sequentially on each subsequently obtained infectious agent-binding nucleic acid or nucleic acid analog are performed at least twelve times. Most preferably, the number of rounds of selection should be determined by the affinity of the selected nucleic acids or nucleic acid analogs to the infectious agent, and these rounds are performed until the binding of the obtained nucleic acid or nucleic acid analog to the infectious agent is not significantly improved (i.e., is less than 20% higher than the binding in the previous cycle).

In another aspect of the method of the invention, the population of infectious agents comprises at least one species of virus. Preferably, the population of infectious agents comprises at least one strain of a species of virus and more preferably, the species of virus is selected from the group consisting of human immunodeficiency virus, hepatitis virus A, hepatitis virus B, hepatitis virus C, hepatitis virus D, hepatitis virus E, herpes simplex virus type 1, herpes simplex virus type 2, varicella zoster virus, Epstein Barr virus, cytomegalovirus, human herpesvirus type 6, human herpesvirus type 7, human papilloma virus, human T cell leukemia virus and *Rous sarcoma* virus.

Also according to the method of the invention, the nucleic acid analog may comprises substituted nucleotide units. Such substituted nucleotide units preferably comprise nucleotide units which confer resistance to nucleases which substitutions are also compatible with reverse transcription and polymerase chain reaction amplification. Preferably, the nucleotide units include substituted pyrimidines, such as 2'-fluoro-pyrimidines including 2'-fluoro-2'deoxycytidine or 2'-fluoro-2'-deoxyuridine residues. The substituted pyrimidines may also comprise 2'-amino-pyrimidine such as 2'-amino-2'-deoxycytidine or 2'-amino-2'-deoxyuridine residues. The nucleotide units may also comprise substituted purines such as 2'-fluoro-purine including 2'-fluoro-2'-deoxyadenine or 2'-fluoro-2'-deoxyguanidine residues. Also included are substituted purines comprising 2'-amino-purine and including 2'-amino-2'deoxyadenine or 2'-amino-2'-deoxyguanidine residues.

In yet another aspect of the method of the invention, the amplified virus-binding RNA is assayed for antiviral activity in an assay selected from the group consisting of a cell culture assay, an enzyme assay, an immunofluorescence assay, a nucleic acid assay and a protein assay.

The invention further includes a method of identifying an antiviral compound comprising the steps of A) incubating a library of RNA or RNA analog molecules in the presence of at least one population of intact viruses to effect binding of the RNA or RNA analog to the viruses; B) separating virus-bound RNA or RNA analog from unbound RNA or RNA analog to obtain a first virus-binding RNA or RNA analog; C) amplifying the first virus-binding RNA or RNA analog; D) incubating the amplified first virus-binding RNA or RNA analog in the presence of at least one population of intact viruses to effect binding of the RNA or RNA analog to the viruses; E) separating amplified virus-bound RNA or RNA analog from amplified unbound RNA or RNA analog to obtain a second virus-binding RNA or RNA analog; F) repeating amplification step C, incubation step D and separation step E until the binding properties of the subsequently obtained virus-binding RNA or RNA analog cannot be significantly improved; and G) assaying the subsequently obtained virus binding RNA or RNA analog for the ability to bind to the virus and inhibit replication of the virus, wherein inhibition of replication of the virus by the subsequently obtained virus-binding RNA or RNA analog is an indication that the subsequently obtained virus-binding RNA or RNA analog is an antiviral compound.

The invention also features a method of preparing an antiviral compound comprising the steps of A) incubating a library of RNA or RNA analog molecules in the presence of at least one population of intact viruses to effect binding of the RNA or RNA analog to the viruses; B) separating virus-bound RNA or RNA analog from unbound RNA or RNA analog to obtain a first virus-binding RNA or RNA analog; C) amplifying the first virus-binding RNA or RNA analog; D) incubating the amplified first virus-binding RNA or RNA analog in the presence of at least one population of intact viruses to effect binding of the RNA or RNA analog to the viruses; E) separating amplified virus-bound RNA or RNA analog from amplified unbound RNA or RNA analog to obtain a second virus-binding RNA; F) repeating amplification step C, incubation step D and separation step E from zero up to about thirty times sequentially on each subsequently obtained virus-binding RNA or RNA analog, or until the binding properties of the subsequently obtained virus-binding RNA or RNA analog cannot be significantly improved; G) assaying the amplified subsequently obtained virus-binding RNA or RNA analog for the ability to bind to the virus and to inhibit replication of the virus, wherein inhibition of replication of the virus by the subsequently obtained virus-binding RNA or RNA analog is an indication that the subsequently obtained virus-binding RNA or RNA analog is an antiviral compound; and, H) isolating and characterizing the subsequently obtained virus-binding RNA or RNA analog.

Also included in the invention is a method of preparing an antiviral compound comprising the steps of A) incubating a library of RNA or RNA analog molecules in the presence of at least one population of intact viruses to effect binding of the RNA or RNA analog to the viruses; B) separating virus-bound RNA or RNA analog from unbound RNA or RNA analog to obtain a first virus-binding RNA or RNA analog; C) amplifying the first virus-binding RNA or RNA analog; D) incubating the amplified first virus-binding RNA or RNA analog in the presence of at least one population of intact viruses to effect binding of the RNA or RNA analog to the viruses; E) separating amplified virus-bound RNA or RNA analog from amplified unbound RNA to obtain a second virus-binding RNA or RNA analog; F) repeating amplification step C, incubation step D and separation step E from zero up to about thirty times sequentially on each subsequently obtained virus-binding RNA or RNA analog, or until the binding properties of the subsequently obtained virus-binding RNA or RNA analog cannot be significantly improved; G) assaying the subsequently obtained virus-binding RNA or RNA analog for the ability to bind to the virus and to inhibit infection of cells by the virus, wherein inhibition of infection of cells by the virus by the subsequently obtained virus-binding RNA or RNA analog is an indication that the subsequently obtained virus-binding RNA or RNA analog is an antiviral compound; and H) isolating and characterizing the subsequently obtained virus-binding RNA or RNA analog.

The invention further features an antiviral composition capable of inhibiting infection by *Rous sarcoma* Virus and an antiviral composition generated by the method of the invention. This antiviral composition directed towards inhibiting infection by *Rous sarcoma* Virus preferably comprises RNA selected from the group consisting of Sequence B, E, F, G and H.

THE DRAWINGS

Figure 4:
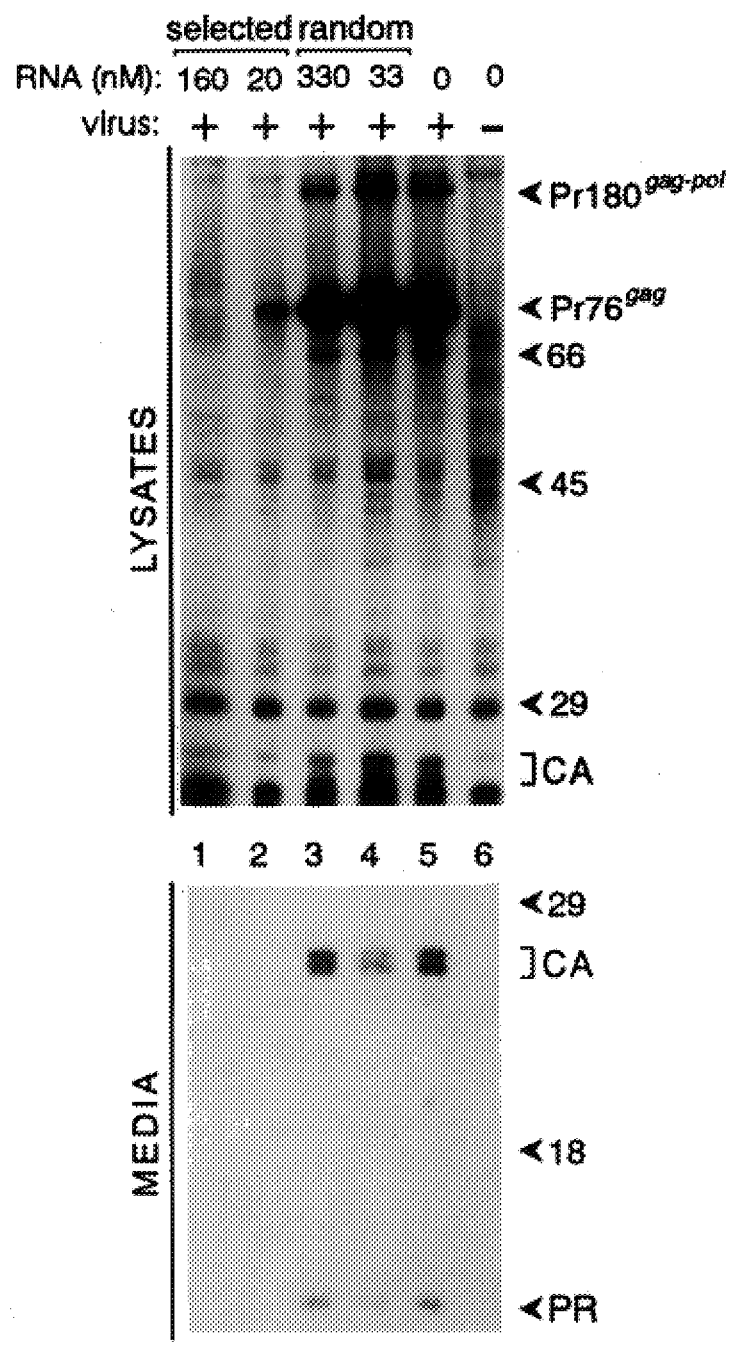

FIG. 4 depicts inhibition of RSV production in QT6 cells by an RNA pool obtained after twelve selection-amplification cycles. RSV (Prague A strain at approximately $10^5$ focus forming units/ml) was supplemented with 2.5 mM MgCl$_2$, mixed with the selected RNA pool and was incubated at 37° C. for 15 minutes. The virus-RNA mixture was placed on 1×10$^6$ QT6 cells, incubated for 1 hour at 37° C. in the presence of 5% CO$_2$ and the medium was then replaced with complete growth medium. At 18 hours post-infection, the cells were labelled with L-[$^{35}$S]methionine for 2 hours. Viral proteins in the cell lysates and media were recovered by immunoprecipitation with anti-RSV serum and were analyzed on 12% polyacrylamide-0.1% SDS gels. Pr76$^{gag}$: full length Gag protein; Pr180$^{gag-pol}$: Gag-Pol fusion protein; CA (capsid) and PR (protease): mature cleavage products derived from Pr76$^{gag}$. The RNA concentration in each sample is shown above each lane.

Figure 5:
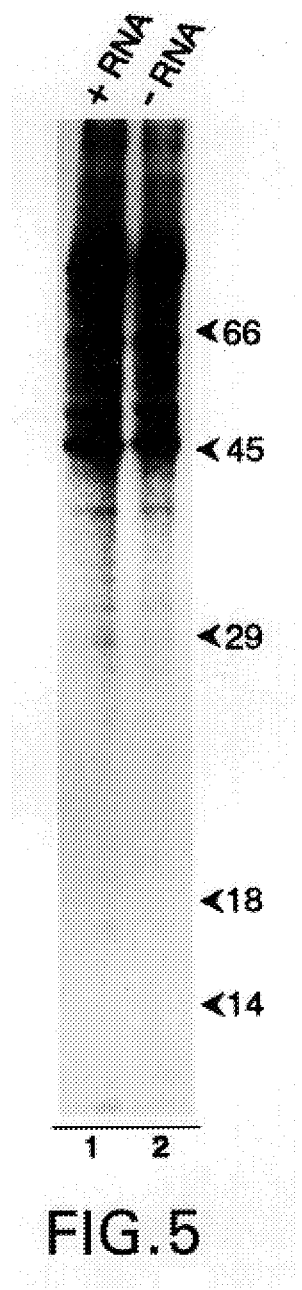

FIG. 5 is a photograph of a gel depicting the effect of the selected RNA pool on host cell protein synthesis. QT6 cells were treated in the absence of RSV with (lane 1) and without (lane 2) 500 nM of the selected RNA pool under the same conditions described for FIG. 4. After radiolabelling, total cellular proteins were analyzed by electrophoresis and autoradiography.

Figure 6A:
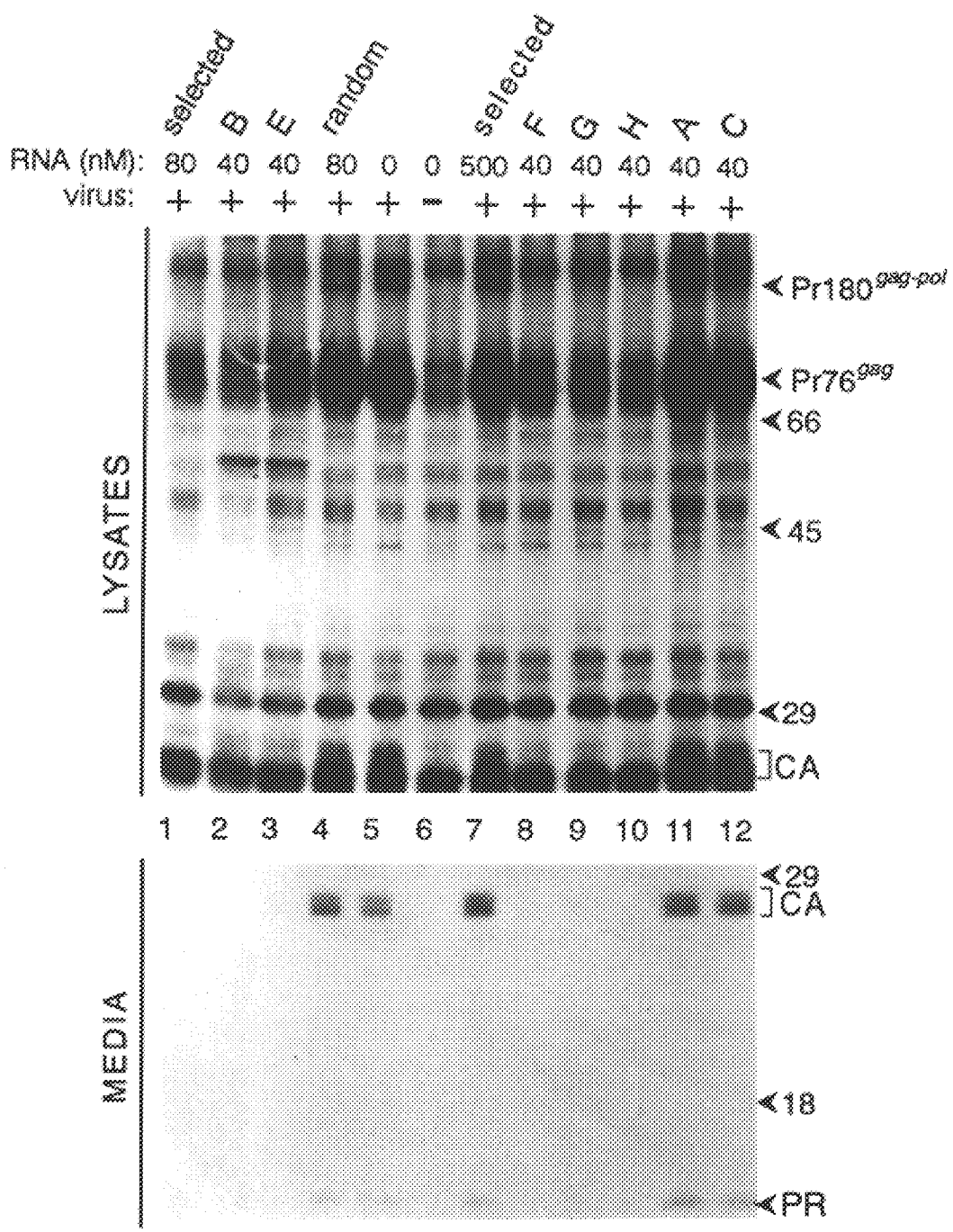

FIG. 6A and 6B, depict inhibition of RSV production by individual RNA sequences. (A) The infections were performed in the same way as described for the selected RNA pool shown in FIG. 5. The symbols used are also as shown in FIG. 5 and the concentration and type of RNA used is shown above each lane. In this experiment, the viral Pr76$^{gag}$ protein overlaps with some background cellular proteins (see lane 6). In lane 7, QT6 cells were treated with the selected RNA pool (500 nM) for 1 hour and were washed with medium prior to infection with RSV. (B) The nucleotide sequences (B, E, F, G and H (SEQ ID NOS:2, 3, 4, 5 and 6, respectively) which inhibit RSV infection are shown. While sequence A (SED ID NO:1) binds both RSV and nitrocellulose membrane and is the most abundant sequence in the selected pool, it does not inhibit RSV infection. Each of the sequences consists of a 5'-fixed region, a variable 40 nucleotide region (uppercase letters), and a 3'-fixed region. Groups of guanosine nucleotides which appear at similar sequences in at least two positions are shown in boldface. The underlined regions are the minimum sequences required for specific binding to RSV as determined by the partial alkaline hydrolysis method (Pan et al., 1992, Biochemistry 31: 3887–3895).

Figure 7:
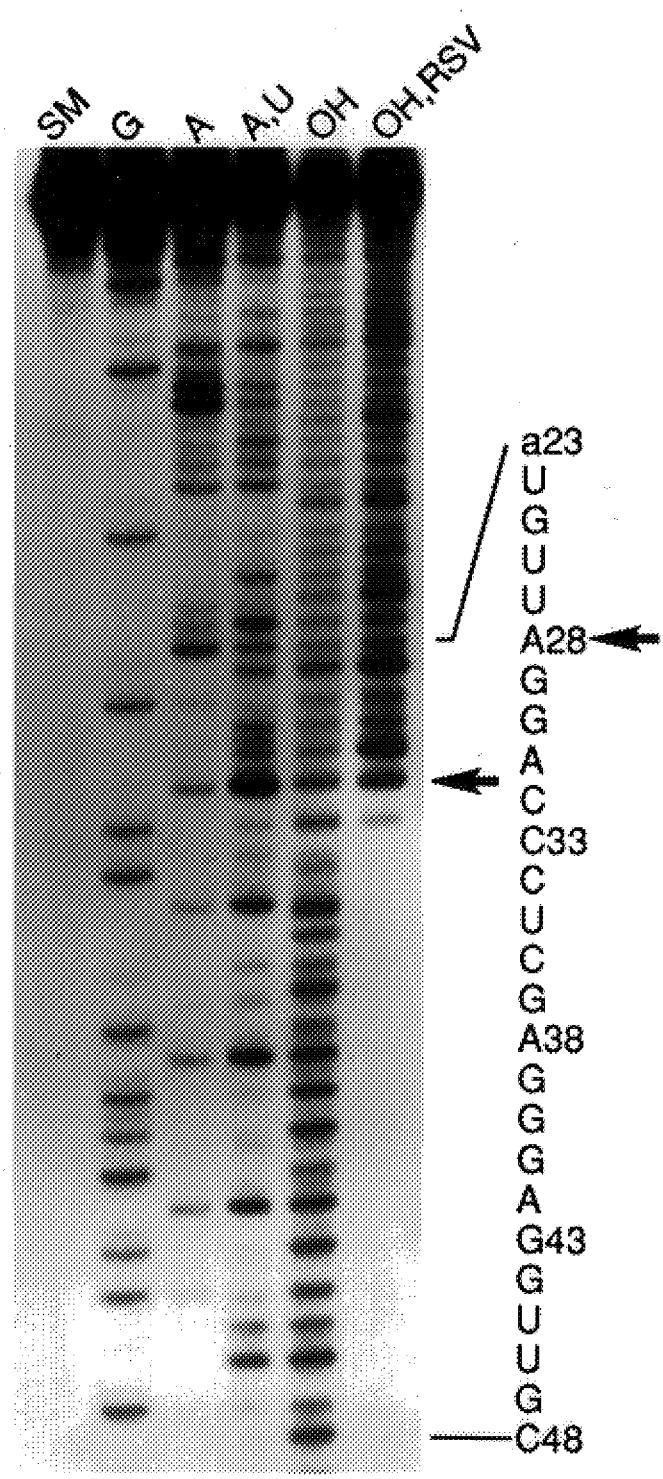

FIG. 7 shows the determination of the minimum sequence requirement SEQ ID No: 7 for binding to RSV:minimal 5'-end determination of sequence H SEQ ID No: 6 . Lane SM is the [3'-$^{32}$P]-labeled sequence H. The G, A, and A,U lanes contain the results of enzymatic sequencing created through the use of ribonucleases T1, U2, and PhyM, respectively. In the lane OH is shown the RNA fragments derived from partial alkaline hydrolysis of sequence H. Lane OH,RSV depicts the fragments which were recovered from binding RSV (3 μg protein/ml). The minimal 5'-end is indicated by arrows. Similar procedures were performed using [5'-$^{32}$P]-labeled RNA to determine the 3'-end boundary.

Figure 8A:
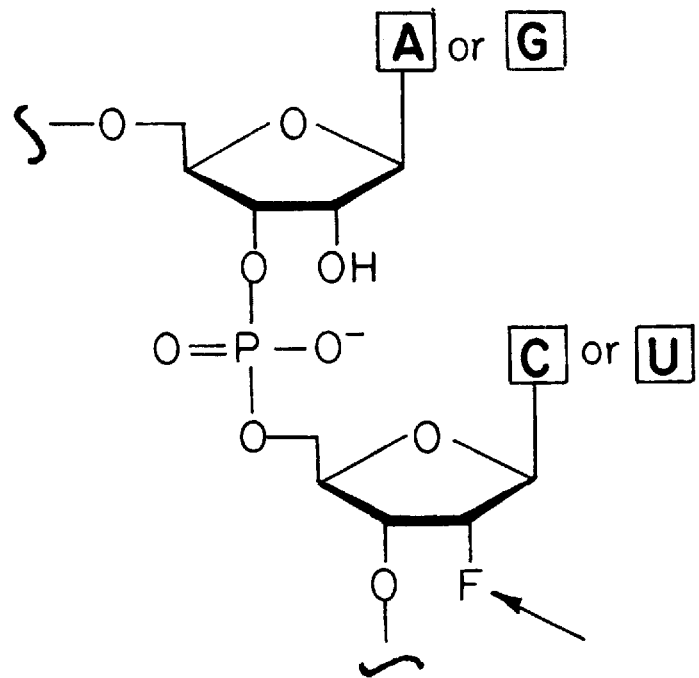
Figure 8B:
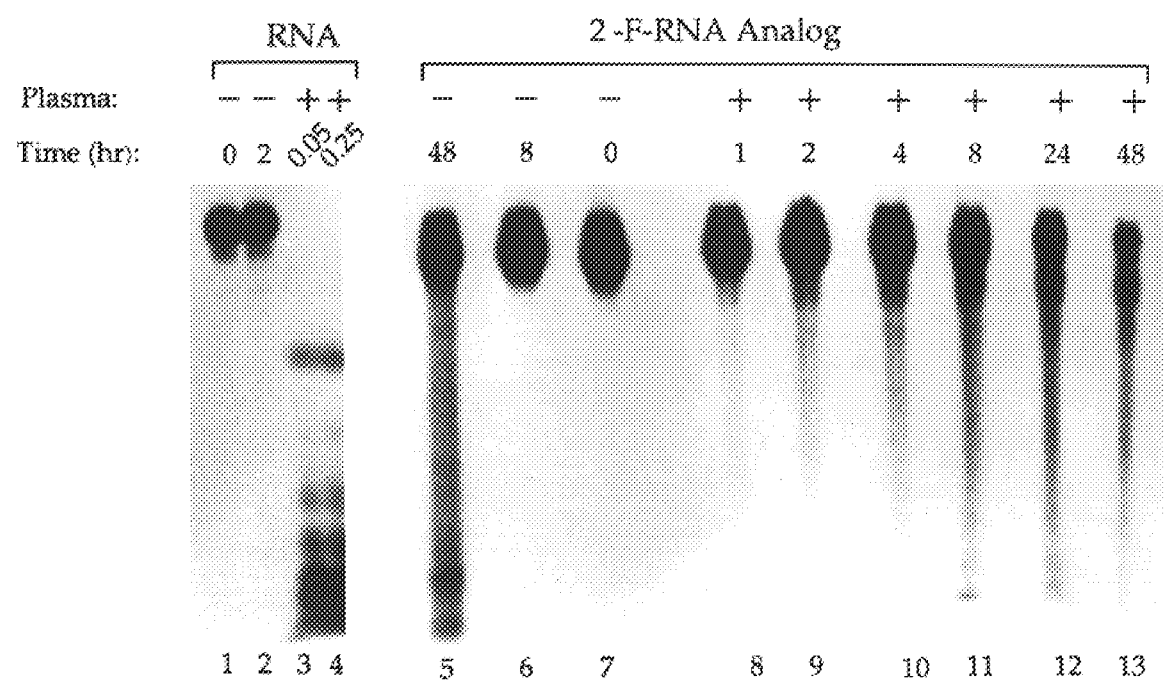
Figure 8C:
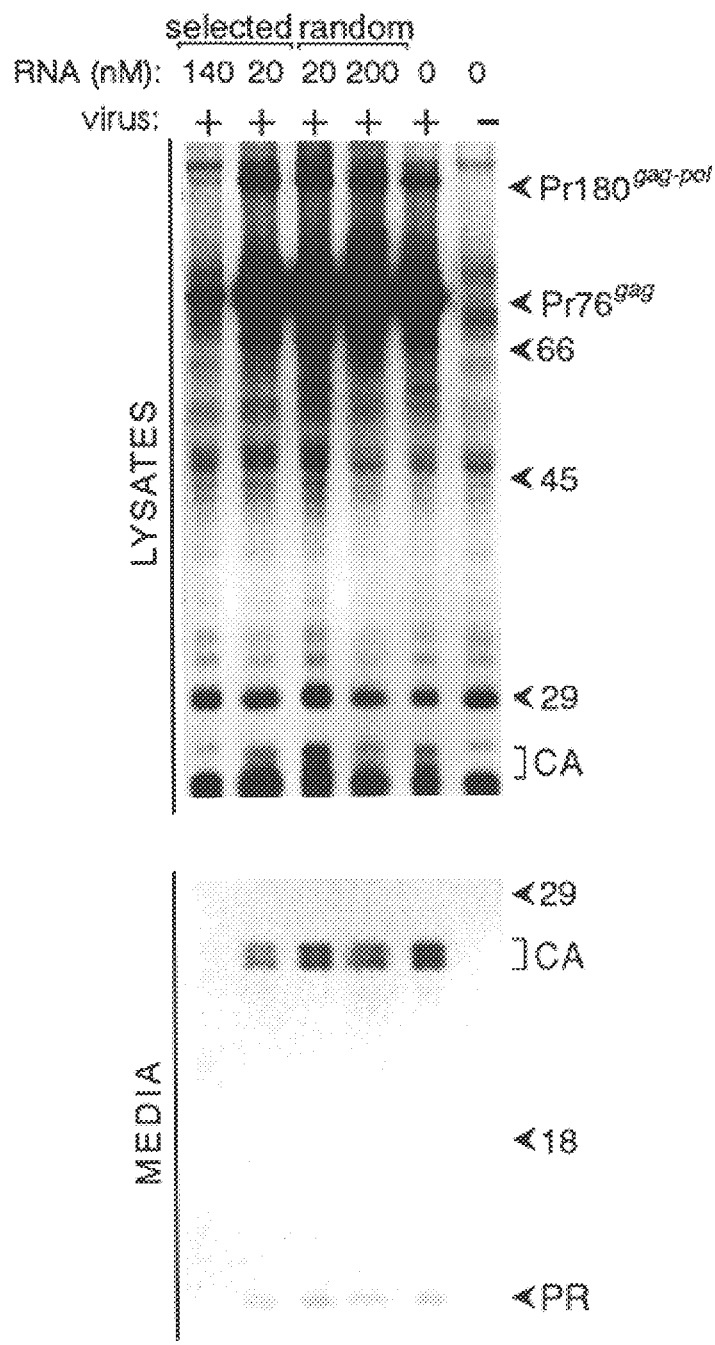

FIG. 8A, 8B, 8C. (A) depicts the structure of 2-'F-pyrimidine-containing RNA analog. (B) is a photograph of a gel depicting the stability of the RNA and the RNA analog of sequence H with regard to its resistance to degradation by nucleases contained within human plasma. The RNA and RNA analog were incubated in the presence of human plasma supplemented with 2.5 MM MgCl$_2$ at 37° C. for the times indicated on the figure. In lane 5 there can be seen Mg$^{2+}$-enhanced hydrolysis at 48 hours. The half-life of the RNA analog in human plasma (22±4 hours) is about the same as those of the analog pools of the selected and random sequences. (C) depicts inhibition of RSV by the analog pool of the same selected sequences shown in FIG. 4.

DETAILED DESCRIPTION

A method has been discovered which facilitates efficient and systematic screening of a large combinatorial library of nucleic acid and nucleic acid analogs for their ability to specifically bind intact infectious agents and to inhibit infection by such infectious agents. This approach thereby provides a new means of diagnosis of infection by infectious agents, and of generating anti-infectious agent compounds.

When the infectious agent is a virus, for example, and the nucleic acid is an RNA or RNA analog, for example, the method of the invention is based upon the premise that binding of a selected RNA or RNA analog to a virus alters the structure of the viral surface proteins so that these proteins can no longer function in steps critical for virus infection, such as virus attachment and virus-cell membrane fusion. In addition, while not wishing to be bound by theory, some of the structural changes induced by RNA binding to virus may also trigger pathways which inhibit steps in virus infection which occur after virus internalization in cells. Such steps include virus uncoating and expression of the viral genome.

The method of the invention should not be construed as being limited to the use of single stranded RNA since single stranded DNA may also be used in the method of the invention. Further, as described below, the method of the invention should not be construed as being limited to viruses; rather, the method of the invention encompasses other infectious agents such as bacteria, fungi such as yeast, and parasites.

The method of the invention comprises a minimum of one selection and one screening step. In the selection step, nucleic acid or analogs thereof (single stranded RNA or DNA or analogs thereof), are selected based upon their ability to bind with high affinity to one particular type of infectious agent or to many different types of infectious agents. In the screening step, nucleic acid or analogs thereof which exhibit the aforementioned binding are assayed for their ability to inhibit infection by the infectious agent.

In the selection step, a modification of the technique of in vitro RNA/DNA mutation-selection-amplification, also known as in vitro evolution is used (Kinzler et al., 1989, Nucl. Acids Res. 17:3645–3653; Joyce, 1989, Gene 82:83–87; Ellington et al., 1990, Nature 346:818–822, Tuerk et al., 1990, Science 249:505–510, each of which are incorporated herein by reference). This technique has heretofore only been used to select for DNA or RNA sequences that bind to isolated proteins, including some viral proteins, small organic molecules and oligonucleotides. According to the method of the invention, it is now possible to modify this technique such that anti-viral compounds directed against intact viruses may be identified.

In the present invention, the technique of in vitro RNA/DNA mutation-selection-amplification is applied to whole, intact biological entities such as infectious agents, i.e., viruses and prokaryotic and eukaryotic cells, and even abnormal cells, such as tumor cells, which are in themselves not infectious. Infectious agents against which the methods of the invention are useful include viruses, bacteria, fungi such as yeast, and parasites. Viruses against which the methods of the invention are useful include human immunodeficiency virus (HIV), hepatitis viruses (for example, A, B, C, D and E), herpes viruses such as herpes simplex virus types 1 and 2, varicella zoster virus, Epstein Barr virus, cytomegalovirus, and human herpesviruses types 6 and 7, human papilloma virus, human T cell leukemia virus and *Rous sarcoma* virus. Although the method of the invention is applicable to all infectious agents, the preferred agents against which the methods of the invention are directed are viruses.

For the purposes of clarity in describing the invention, viruses will be used as examples of the infectious agent and RNA or RNA analogs will be used as examples of the nucleic acid or nucleic acid analog. With this in mind, to perform the method of the invention, a library of nucleic acid molecules of different sequences is first generated using an oligonucleotide synthesizer. The library comprises oligonucleotides having from about 40 and about 450 nucleotide units contained therein. The oligonucleotides may comprise a length of any and all increments between 40 and 450 nucleotide units. DNA templates for synthesis of longer oligonucleotides may be obtained by ligating several DNA fragments together (Bartol et al., 1993, Science 261:1411–1418). Preferably, the library comprises oligonucleotides having between about 50 and 250 nucleotide units contained therein. More preferably, the library may comprise oligonucleotides having any number of nucleotide units between about 50 and about 150. Most preferably, the library comprises oligonucleotides having about 75–95 nucleotide units.

The library is generated by randomizing the sequence of a core set of nucleotide units within each starting oligonucleotide. The core set of nucleotides to be randomized may comprise as many as 350 and as few as 10 nucleotide units and any and all increments therebetween. Preferably, the core set of nucleotides to be randomized comprises about 30–40 nucleotides having about 20 additional nucleotides at each of the 5' and 3' ends of the sequence. Thus, the starting (unselected or random) pool of oligonucleotides of the invention contain a core sequence region having a random sequence and a constant sequence region at each of the 5' and 3' ends of the molecule, wherein the 5' sequences are identical to each other and the 3' sequences are identical to each other and the 5' and 3' sequences are not necessarily identical to each other.

Oligonucleotides within the random pool of oligonucleotides generated as described above, are next selected for their ability to bind to the test virus. Oligonucleotides within this pool which are not selected as described below are termed "random" oligonucleotides, whereas those which are selected as described below are termed "selected" oligonucleotides. An unselected pool of oligonucleotides (random) serves as a control in the experiments described below.

For selection, the oligonucleotides are incubated in the presence of the subject virus under physiological conditions to effect binding of the nucleic acids to the virus. Such conditions include a pH buffer (e.g., phosphate buffered saline: PBS) and salts (e.g., Earle's salt solution). Oligonucleotides which bind virus are separated from unbound oligonucleotides by filtration, centrifugation, chromatography or other means which effects such separation. Virus-bound oligonucleotides are eluted from the virus by the addition of EDTA and urea and extraction with phenol:chloroform.

Oligonucleotides so obtained are then reverse transcribed to DNA and are amplified using PCR technology (ordinary or mutagenic PCR) using primers which bind to the constant regions at the 5' and 3' ends of the DNA oligonucleotides. RNAs that are subscribed from the DNA oligonucleotides so amplified are then incubated with virus under the same conditions described above to effect binding of the RNA to the virus. RNAs which bind during the second round of binding are separated from unbound RNAs and are again reverse transcribed and are amplified by PCR. Multiple cycles of amplification and binding may be conducted wherein RNAs are generated which have increasing binding affinity for the subject virus. Selection for increased binding affinity is effected by reducing the amount of virus available for binding during each cycle. The cycles of amplification and selection will continue until the binding properties of the subsequently obtained RNAs to the virus can no longer be significantly improved. The number of cycles required to generate RNAs which bind with high affinity to any given virus will depend on the nature of the oligonucleotides within the starting pool and on the type and quantity of virus available for binding. Thus, high affinity binding RNAs may be generated in a single cycle of selection or in any number of additional cycles of selection up to even as many as thirty cycles, perhaps even more, and any number of cycles between one and greater than thirty cycles. The preferred range of selection cycles is from about five to about twenty cycles. The actual number of selection cycles to be performed will be the number needed to achieve the maximum binding affinity between the subsequently obtained RNA or RNA analog and the virus. When further selection can no longer improve the affinity of the RNA pool to the virus the selected RNA pool is tested for its ability to inhibit infection by the virus. The RNA having antiviral activity are then cloned and sequenced in order to generate large quantities for additional testing and/or modification.

It is not necessary that the RNAs be selected by binding to one single type of virus. In fact, the selection for virus-binding RNAs may be performed with alternating different viruses in different cycles. The method of the invention should therefore be construed to include any and all combinations of viruses and cycles. For example, the selection may be performed using virus A, in cycles 1, 4, and 7, virus B in cycles 2, 5, and 8, and virus C in cycles 3, 6, and 9, etc. It is expected that the resulting RNAs will be capable of binding to all three viruses. In addition, in the case of viruses such as HIV which have a high mutation rate, selection may be performed using multiple strains of viruses in various combinations. It is expected that such selection would yield RNAs capable of binding to the more conservative motifs contained within the viral proteins thereby resulting in RNAs having a potentially broad range of antiviral activity, i.e., being effective in inhibition of replication of several HIV strains. Selections which are performed in this manner may generate antiviral RNAs to which the virus is less apt to develop resistance, thereby overcoming the significant drug resistance problems which are frequently associated with conventional therapeutic approaches to development of antiviral agents. Selection for RNAs that are effective against diverse viral strains is both possible and practical using the method of the invention since a very large structurally diverse library of RNAs are used in what amounts to a very rapid selection process.

In the second step of the method of the invention, RNAs which bind to intact viruses are tested for antiviral activity in conventional cell culture assays and in animal models. In the former case, the test compound is added to cells either prior to, in conjunction with, or following virus infection of the same. Assays for virus replication include cytotoxic cell assays, plaque assays, colony forming assays, virus enzyme production and assessment of general or specific virus macromolecular synthesis using any number of techniques available to those skilled in the art including DNA, RNA and protein synthesis. The type of assay to be used will depend on the type of virus being tested and will be readily apparent to the skilled artisan (Fields et al, 1989, Virology, Raven Pres, NY, which is incorporated herein by reference).

By intact virus is meant virus which has not been disrupted using chemical or physical agents. Intact virus should be construed to include all viruses within a population of viruses harvested from cells in which the virus was replicated. This term therefore includes both infectious and non-infectious particles since it is well known that populations of viruses harvested from cells comprise both entities.

Animal studies to assess actual inhibition of virus replication in a host are also well known to the skilled artisan. In this instance also, the type of animal and assay to be used will depend on the type of virus being tested and will be readily apparent to the skilled artisan (Fields et al, 1989, Virology, Raven Pres, NY). For example, anti-HIV compounds may be tested in the SCID-hu mouse model, a small animal model for HIV infection of human tissues. This model is commonly used for evaluation of potential anti-HIV agents (McCune et al., 1990, Science 247:564–566, which is incorporated herein by reference). Other animal models for other viral infections are described in Fields et al. (1989, Virology, Raven Pres, NY) and in the references described therein.

Methods of administration of antiviral compounds identified following the method of the invention are also known to those skilled in the art and depend upon the type of virus, the infection being treated and the state of the host. Antiviral agents generated by the method of the invention may be administered to a human or another animal in one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). The compounds can be administered to the human in a dosage of 0.1 $\mu$g/kg/day to 50 mg/kg/day, either daily or at intervals sufficient to inhibit virus replication and diminish or ablate virus induced disease in the host. Precise formulations and dosages may be determined using standard techniques, by a pharmacologist of ordinary skill in the art.

The method of the invention is generally applicable for the development of compositions effective against many, if not all viruses and other microorganisms, such as bacteria and other cells. Viruses for which the methods of the invention are useful include all viruses capable of infecting and causing disease in humans and animals including those viruses described in Fields et al. (1989, Virology, Raven Press, NY).

Viruses for use in binding assays may be prepared also according to methods readily available in the art. Generally, preparations of viruses are obtained by infecting either cells in culture, tissues ex vivo, or eggs or animals capable of replicating the virus. After a proscribed period of time, the virus is harvested from infected host cells and is used directly in the binding assay described herein, or is further purified, using ordinary virus purification techniques, referenced, for example, in Fields et al. (1989, Virology, Raven Press, NY), prior to the binding assay.

RNA or RNA analogs which have antiviral activity may be further modified by chemical modification, in order to enhance their stability, i.e., resistance to nucleases. Modification of RNA may be performed either prior to or following identification of the RNA as having antiviral activity. Such modifications of RNA are now well known to those skilled in traditional antisense oligonucleotide technology and are described, for example, in Eckstein (1991, Oligonucleotides and Analogues, A Practical Approach, Oxford University Press, Oxford, England) and in Crooke et al. (1993, Antisense Research and Applications, CRC Press) both of which are herein incorporated by reference. Chemically modified oligonucleotides include those which comprise phosphorothioate, phosphotriester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No.:5,034,506, herein incorporated by reference) or polyamide backbone structures (Nielsen et al., 1991, Science 254: 1497, herein incorporated by reference) may also be used. The examples of oligonucleotide modifications described herein are not exhaustive and it is understood that additional modifications of the oligonucleotides generated according to the methods of the invention, which modifications serve to enhance the therapeutic properties of the oligonucleotide without appreciable alteration of the basic sequence of the oligonucleotide are also included.

In addition to the aforementioned modifications of RNA or RNA analogs, substituted nucleotides may also be used during synthesis of the RNAs in any one or all of the selection cycles to generate modified RNAs. Such nucleotides include, but are not limited to 2'-fluoro-pyrimidines and 2'-amino-pyrimidines, 2'-fluoro-purines and 2'-amino-purines. The invention includes 2'-fluoro-pyrimidines such as 2'-fluoro-2'-deoxycytidine and 2'-fluoro-2'-deoxyuridine residues, 2'-amino-pyrimidines such as 2'-amino-2'-deoxycytidine or 2'-amino-2'-deoxyuridine residues, 2'-fluoro-purines such as 2'-fluoro-2'-deoxyadenine or 2'-fluoro-2'-deoxyguanidine residues, and 2'-amino-purines such as 2'-amino-2'deoxyadenine or 2'-amino-2'-deoxyguanidine residues.

Thus, the invention should be construed to include RNA analogs in addition to unmodified RNA sequences. By the term RNA analog is meant an RNA sequence which contains nucleoside subunits which have been chemically modified which modifications confer properties upon that RNA which enhance the antiviral effect of the RNA. Such enhancement includes improved stability of the RNA in addition to improved ability to bind the target virus and effect inhibition of replication thereof.

RNAs which exhibit virus binding and virus infection and replication inhibition activity may be cloned in the form of cDNAs, sequenced and then be subsequently modified as discussed herein. The RNAs which are generated according to the methods of the invention may also be modified by mutation, which mutated sequences may be further selected by binding to intact virus and subsequently tested for improved virus binding and antiviral activity in the assays described herein. Modification by mutation includes mutation by PCR, conventional site directed mutagenesis and other common mutation methods which are described for example in Sambrook et al. (Molecular Cloning, A Laboratory Manual, Cold Spring Harbor, N.Y.). The invention should therefore be construed to include RNAs generated according to the methods of the invention and all analogs and homologs thereof.

Homologs of such RNA or RNA analogs may also be useful as antiviral agents. Homology between two nucleic acid molecules refers to the subunit sequence similarity between the two nucleic acid molecules. When a subunit position in both of the two molecules is occupied by the same monomeric subunit (e.g., if a position in each of two nucleic acid molecules is occupied by adenine), then they are homologous at that position. The homology between two sequences is a direct function of the number of identically matching or homologous positions, e.g., if half (e.g., 5 positions in a polymer 10 subunits in length) of the positions in two nucleic acid sequences match, then the two sequences are 50% homologous; if 70% of the positions, (e.g., 7 out of 10), are match, then the two sequences share 70% homology. By way of example, the nucleic acid sequences GAATTC and GAAGGT share 50% homology.

Preferably, homologs of RNAs generated according to the methods of the invention include those which share at least about 40% sequence homology with the RNAs so generated. More preferably, homologs which are useful include those which share at least about 50%, more preferably at least about 60%, even more preferably at least about 70% and most preferably at least about 80% homology with the originally selected RNAs.

The method of the invention may also be used to select for nucleic acid analogs which have defined pharmacological lifetimes and are effective against multiple strains of viruses. It has been discovered that RNAs containing 2'-fluoro-nucleotides are more resistant to nucleases present in human plasma than their unmodified counterparts (see Example 9 described herein). Since the half-life of the RNAs in human plasma is dependent upon the number of 2'-fluoro-pyrimidine residues contained within the RNA, it is possible to control the RNA half-life by controlling the number of 2'-fluoro-pyrimidine resides contained therein.

Thus, according to the method of the invention, RNA and RNA analogs are selected from a large combinatorial library by their ability to bind intact virus and to inhibit virus infection. This method is exemplified below wherein RNAs and analogs thereof were identified which bound to and inhibited replication of *Rous sarcoma* virus (RSV).

The advantages of using in vitro RNA/DNA mutation-selection-amplification as it applies to whole biological entities compared with its use as applied to isolated proteins, are many. In the first instance, since it is the virus rather than any one protein isolated therefrom which causes the disease, by targeting intact viruses and virus infected cells as a means of identifying antiviral agents, potentially many more candidate antiviral agents are identified. Moreover, a viral protein may assume several different structural conformations depending upon whether it is associated with an intact virion, an infected cell, or whether it is in partially or fully isolated form. Thus, the RNA which is selected to bind an isolated form of a protein may or may not interact with that protein when it is complexed with other viral or cellular components. Since, in order to effect inhibition of virus replication it is necessary that the selected RNA interact with the viral protein in its natural state, by requiring that the RNA being selected interact with viral proteins as they are associated with whole virus or infected cells, again, potentially many more candidate antiviral agents are identified. A further advantage to the application of in vitro RNA/DNA mutation-selection-amplification to whole viruses is that the actual selection of RNAs for their ability to bind intact virus can be performed under physiologically more relevant conditions comparable to those present during infection of cells by viruses.

Yet another advantage of the technique of the instant invention is derived from the fact that selection of RNAs for binding to intact virus does not require that there be a detailed understanding of the complex mechanisms involved in virus-cell interactions during virus infection and replication. This is particularly important for the identification of agents having antiviral activity directed against viruses such as HIV, wherein such virus-cell interactions remain largely an enigma despite intensive study. Thus, selection for RNA or RNA analogs having antiviral activity using intact virus permits the development of antiviral RNA and RNA analogs absent a complete knowledge of the mechanisms governing viral infection, replication and/or inhibition of the same.

In yet another advantage of the method of the instant invention, it is not necessary that large quantities of viral proteins be purified in order to perform the method. Rather, simple preparations of viruses may be obtained from cells infected with such viruses.

Accordingly, the method of the invention has significant advantages over conventional screening techniques for the identification of antiviral agents and overcomes the numerous difficulties associated with the selection using isolated viral proteins. The method of the invention therefore provides a new and effective means for the development of antiviral agents.

The invention is further described in the following examples. These examples are illustrative only and are not intended to limit the scope of the appended claims.

EXAMPLES

Example 1. Generation of a Large Pool of Combinatorial RNA Sequences

Figure 1:
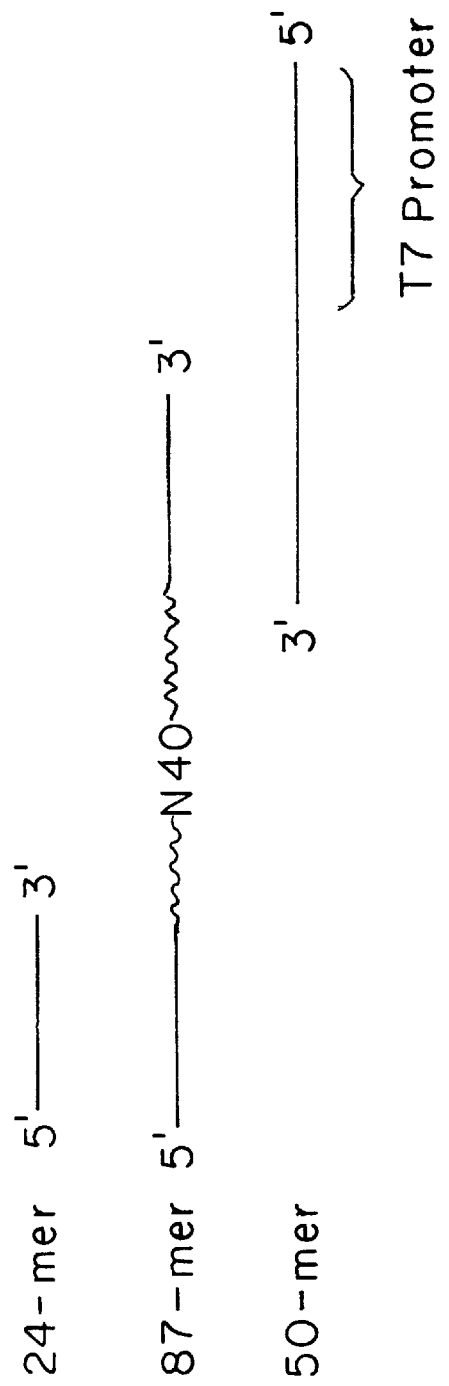
FIG. 1 is a diagram depicting the design of DNA oligonucleotide libraries and PCR primers. N40 is a variable region of 40 nucleotides wherein the identity of each nucleotide is completely random.

A DNA library containing approximately $5 \times 10^{16}$ sequences (2.5 mg DNA) was constructed by automated solid-state synthesis at the Core Facilities of Hershey Medical Center. Sequence diversity within the library was generated by randomizing a 40-nucleotide region of an 87-nucleotide oligomer (FIG. 1). The non-randomized portion of the oligonucleotide comprises a nucleotide sequence which does not share homology with the genome sequence of the virus to which the RNA is to be bound. Two oligonucleotide primers having 24 (24-mer) and 50 (50-mer) nucleotides, respectively, were also generated on the same DNA synthesizer. These oligonucleotides were used in polymerase chain reactions (PCR) described below. The 50-mer contains a promoter for T7 RNA polymerase (T7 promoter) and the 24-mer comprises a nucleotide sequence which is not homologous to the genome of the virus to which the RNA will be bound. Large scale PCR of the DNA library resulted in the generation of approximately $5 \times 10^{15}$ double stranded DNA (dsDNA) sequences which were transcribed by T7 RNA polymerase to generate a pool of multiple copies of approximately $10^{15}$ RNA sequences (random pool).

Example 2. Selection for RSV-binding RNA Sequences

The RNAs contained within the pool generated as described in Example 1 were subjected to selection for their ability to bind the Prague A strain of *Rous sarcoma* virus (RSV). The selection was performed by incubating the RNA pool, at a concentration of 2.5 mg RNA/1.5 ml, in the presence of RSV in a solution containing 2.5 mM $Mg^{2+}$, 100 mM NaCl, 20 mM Tris, pH 7.5 at 37° C. for 10 minutes. The concentration of virus used was approximately 30 µg/1.5 ml. Virus was purified by ultracentrifugation through a sucrose gradient following propagation in turkey cells. Unbound RNA was separated from virion bound RNA by filtration through a nitrocellulose membrane. RNA bound to virus was recovered from the membrane by denaturing the RNA-RSV complexes through the addition of 10 mM EDTA to chelate $Mg^{2+}$ and to denature the RNA. Urea (8M) was also added and viral proteins were removed by phenol-chloroform extraction. RNA preparations so obtained were precipitated with ethanol.

The RNA molecules which bound material other than RSV (e.g., the nitrocellulose membrane, cellular proteins attached to viral surfaces, etc.) were removed from the RNA pool by background selection performed either prior to or after incubation with virus. The RNA pool was incubated in the presence of cells and was subsequently filtered through a nitrocellulose membrane. RNA which passed through the membrane was used for selection with virus. RNAs which were retained by the membrane were discarded.

As an added optional step, RNA-virus complexes were separated from the unbound RNA by high-speed centrifugation wherein the RNA-virus complexes were caused to pellet along with the unbound virus while the unbound RNA remained in the supernatant. The RNA-RSV complexes were then denatured and viral proteins were removed from the RNA using phenol and chloroform. The RNA was recovered by ethanol precipitation.

Example 3. Generation of cDNA Complementary to the Selected RNAs

RNA sequences which bound RSV were subsequently used as templates for the generation of cDNA using reverse transcriptase in the presence of the 24-mer as primer (FIG. 1). Reverse transcription was performed at 48° C. for 1 hour using SuperScript II reverse transcriptase obtained from Gibco/BRL.

Example 4. PCR of cDNA and Generation of a Subsequent Pool of RNA to be Used in an Additional Selection Cycle Complementary DNA molecules generated as described above were used as templates for the synthesis and amplification of additional dsDNA molecules. This was accomplished by incubating the cDNA in the presence of both the 24-mer and 50-mer primers. It was possible to introduce a low rate of mutation (e.g., about 1%) into the DNA during the PCR reaction by performing PCR under non-biased error-prone conditions (0.2 mM DATP and dGTP, 1 mM dCTP and dTTP, 7 mM $MgCl_2$, 0.5 mM $MnCl_2$, 2X Taq polymerase). Mutation of the cDNAs under these conditions is approximately random and occurs at a rate of approximately 0.66 to 1.1% (Cadwell et al., 1992, PCR Methods Appl. 2:28–33).

PCR-amplified dsDNA molecules were then used as templates in a transcription reaction giving rise to a new pool of RNA further enriched for RSV-binding sequences. The transcription reaction is also an amplification process in that up to about 200 copies of RNA were obtained from each DNA template incubated in the presence of T7 RNA polymerase and the appropriate nucleotides. The RNA pool so generated was then incubated in the presence of intact RSV. RNAs which bound RSV were isolated as described herein. For each cycle of selection, the stringency of the assay was increased by using progressively less RSV during each round of selection. Approximately 6 to 15 cycles were performed using a concentration of RSV ranging from 30 μg viral protein per 1.5 ml in cycle one to 2 μg viral protein per 1.5 ml in cycle twelve.

Example 5. Enrichment for High Affinity RSV-binding RNA Sequences

Figure 2:
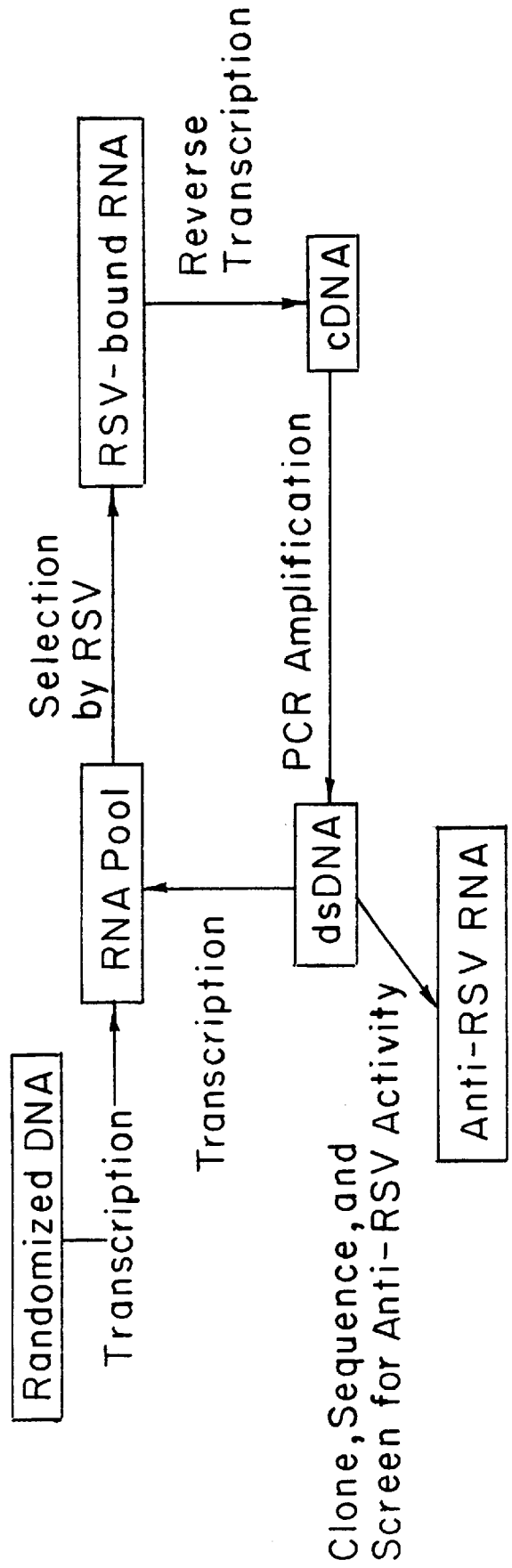
FIG. 2 is a schematic diagram of in vitro screening of a combinatorial library of RNA and RNA analogs for their ability to bind virus.
Figure 3:
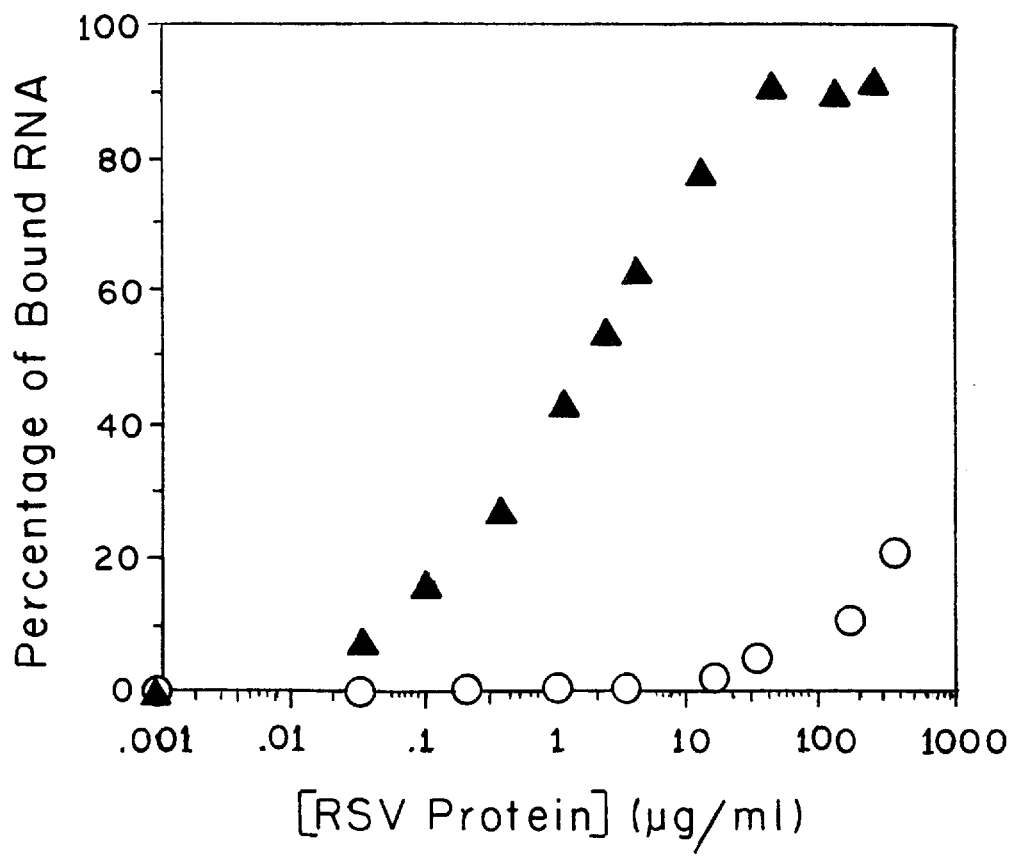
FIG. 3 is a graph depicting binding of Rous sarcoma virus (RSV) to 0.2 to 0.5 nM of a $^{32}$P-labeled selected RNA pool obtained after twelve selection-amplification cycles (solid triangles), and a random RNA pool (open circles).

Multiple cycles of mutation, selection and amplification resulted in an exponential increase in the number of RNAs having a high affinity for RSV (FIG. 2). Following twelve cycles of selection and amplification, the dissociation constant (Kd) of RSV bound to the selected RNA pool decreased to approximately 3 μg/ml, which is at least 1000 times less than that measured with the starting RNA pool of random sequences. More cycles of amplification and selection lead to no measurable improvement in the affinity between the selected RNA pool and RSV. RNAs in the selected pool were thus sequenced and it was evident that particular sequences were present at a high frequency in this RNA population.

Example 6. Assessment of the Ability of RNAs Contained Within the Selected RNA Pool to Inhibit Virus Replication and Infection RNAs within the selected RNA pool were incubated in the presence of RSV for 10–15 minutes at 37° C. in 20 mM Tris, pH 7.5, 100 mM NaCl, 2.5 mM $MgCl_2$, at the RNA and RSV concentrations indicated in FIG. 4, followed by incubating the RNA-virus mixture with approximately $10^6$ QT6 cells in a $CO_2$ incubator (37° C., 5% $CO_2$) for 1 hour. The unabsorbed RNA and viruses were removed by washing and the cells were incubated in F-10 medium (Gibco BRL) containing 2 mM $MgCl_2$ for 24–38 hours. The QT6 cells were then metabolically labeled with L-[$^{35}$S]methionine for approximately 2 hours. To obtain viral proteins, growth medium was separated from the infected cells and proteins were extracted from both the medium and the cells in the presence of protease inhibitors. Virus specific gag proteins were immunoprecipitated at 4° C. using rabbit antiserum directed against intact RSV. Immunoprecipitated proteins were separated by electrophoresis through 10% polyacrylamide, 0.1% SDS and protein bands were visualized by fluorography using Fluoro-Hance (Research Products International, Inc.) and Kodak X-Omat ARS film (FIGS. 4, 5 and 6). As a control, the random RNA pool was also tested in the same way for its effect on RSV infection and replication.

In the absence of any added RNA, efficient virus infection and replication in QT6 cells was evidenced by the presence of large amounts of full-length gag proteins (i.e., mature gag $Pr76^{gag}$ and gag-pol precursor $Pr180^{gag-pol}$) in cell lysates and the presence of capsid proteins (CA) and viral protease (PR) in the growth medium (see lane 5 of FIG. 4). Background bands evident in FIGS. 4 and 6 are cellular proteins which were nonspecifically precipitated by the antiserum. When RNAs from the random RNA pool (up to a final concentration of 330 nM of RNA) were present in the reaction, the production of either viral or cellular proteins (such as the 29 kDa band) was unaffected (FIG. 4, lanes 3 and 4). In contrast, use of 20 nM of the selected RNA pool reduced the yield of viral proteins by 85–92% (FIG. 4, lane 2, estimated by densitometry). When a selected RNA pool concentration of 160 nM was used, the production of RSV was completely inhibited (FIG. 4, lane 1). The selected RNA pool did not affect the production of cellular proteins to any detectable extent (compare the background bands in lane 1 and 2 with those in lane 5 of FIG. 4). Thus, the observed inhibition of virus production in cells infected by the selected RNA pool bound virus is specific for RSV in that cellular protein production was unaffected in these cells.

To further examine the effect of the RNAs from the selected RNA pool on the growth of QT6 cells and on their susceptibility to infection by virus, protein production in these cells was assessed as a measure of the incorporation of [$^{35}$]-methionine therein. It is evident from the data shown in FIG. 5, lanes 1 and 2 that the quantity of [$^{35}$S]-labeled cellular proteins in QT6 cells was unaffected by the addition to the cells of 500 nM of RNA from the selected RNA pool.

This result confirms the fact that RNAs from the selected RNA pool, similar to those obtained from the random RNA pool, have no effect on growth of the host cells. Furthermore, when the host cells were treated for 1 hour with 500 nM of RNA obtained from the selected RNA pool (500 nM), washed with medium and then subsequently were infected with RSV, no effect on the yield of the viral proteins was observed (compare lane 7 with lane 5 of FIG. 6A). These data thus establish that RNAs obtained from the selected RNA pool had no effect on the susceptibility of QT6 cells to infection with RSV.

RNAs within the selected RNA pool which were selected for binding to the Prague A strain of RSV, were also effective in inhibiting replication of the Prague C strain of RSV. The RNA concentration required to inhibit the Prague C strain was about 15–20 times higher (e.g., 260 nM compared with 15 nM) than that required to achieve the same level of inhibition (about 80%) of the Prague A strain of RSV. The surface glycoprotein (gp85) of these two strains contains conserved regions (there is approximately 95% homology between these two regions) as well as 3–4 small variable regions (subgroup-determining regions). While not wishing to be bound by theory, if the selected RNAs and analogs neutralize virus by interaction with the surface glycoprotein, it is likely that a small number (e.g., approximately 5% ) of the Prague A neutralizing sequences in the selected pool will bind to the conserved regions in the Prague C strain thereby also neutralizing this virus. These data demonstrate that RNAs selected against one particular virus may in fact be effective in inhibiting the replication of other related viruses.

Example 7. Cloning of high Affinity RSV-binding and RSV-inhibiting RNA Sequences DNA copies of RNAs contained within the twelve-cycle generated selected RNA pool were cloned to the well-known vector pUC19. Thirty six of the clones so generated were sequenced using conventional sequence technology. Some consensus sequences were observed among the clones. The most dominant sequence (sequence A SEQ ID No: 1) appeared in nine clones; sequences B (SEQ ID NO: 2), C, D and E (SEQ ID NO: 3) were observed in four, four, three and two clones, respectively. Each of the remaining fourteen clones comprised unique sequences. Among nineteen of the sequences identified within the thirty six clones, five sequences (B, (SEQ ID NO: 2), E, (SEQ ID NO: 3), F, (SEQ ID NO: 4), G, (SEQ ID NO: 5), H (SEQ ID NO: 6)) inhibited RSV infection and replication (FIG. 6).

In the experiment shown in FIG. 6, migration of the viral protein Pr76$^{gag}$ overlaps with that of cellular proteins. This overlap varies from experiment to experiment (lane 6). Thus, a better measure of RSV production among the various lanes in FIG. 6A is accomplished by comparing the yield of Pr180$^{gag-pol}$ in cell lysates and the yield of CA and PR in the medium among the various lanes. From the data presented in FIG. 6A it can be seen that 40 nM of sequences E (SEQ ID NO: 3), F (SEQ ID NO: 4) and G (SEQ ID NO: 5) inhibited RSV as effectively as 80 nM of the selected RNA pool (compare lanes 3, 8 and 9 to lane 1 of FIG. 6A). Side by side experiments established that sequences B (SEQ ID NO: 2) and H (SEQ ID NO: 6) were two- to three-fold as effective in neutralizing RSV compared with sequences E (SEQ ID NO: 3), F (SEQ ID NO: 4) and G (SEQ ID NO: 5). Sequence A (SEQ ID NO: 1) bound to RSV with an affinity comparable to that of sequences B (SEQ ID NO: 2) and H (SEQ ID NO: 6) ($K_d$ approximately 2–3 µg viral protein/ml); However, sequence A (SEQ ID NO: 1) also had at least a four times higher affinity for nitrocellulose membrane than did sequences B (SEQ ID NO: 2) and H (SEQ ID NO: 6).

A comparison of the nucleotide sequence of the cloned sequences revealed that groups of guanosine nucleotides appeared at similar positions in all of the RSV-neutralizing RNA sequences (FIG. 6B). Despite this fact, there appeared to be no consensus among the secondary structure (base-pairing) diagrams of these sequences which were generated by energy minimization.

Example 8. Identification of the Minimum Sequences Required for Binding and Inhibiting RSV Systematic deletion of nucleotides from both the 5' and 3' ends of each of the sequences identified above demonstrated that a 42-nucleotide region of B (SEQ ID NO: 2), a 20-nucleotide region of E (SEQ ID NO: 3), a 35-nucleotide region of F (SEQ ID NO: 4), a 38-nucleotide region of G (SEQ ID NO: 5) and a 28-nucleotide region of H (SEQ ID NO: 6) were sufficient for binding RSV (FIG. 7). These regions are underlined in FIG. 6.

Example 9. Nuclease Resistance of Modified Selected RNA Sequences in Human Plasma Unmodified RNAs are susceptible to degradation by nucleases, thus, in some instances, their use as therapeutic agents may be limited. However, incorporation of modified nucleotides into an RNA chain easily circumvents this problem. For example, the incorporation of 2'-fluoro-2'-deoxycytidine and 2'-fluoro-2'-deoxyuridine into an RNA chain is easily accomplished in an in vitro transcription reaction using T7 polymerase. The structure of a 2'-fluoro-pyrimidine RNA analog is shown in FIG. 8A. Modified RNAs so generated exhibit enhanced resistance to nuclease digestion (FIG. 8B). Comparable increases in RNA stability are observed using sequence H or RNA obtained from random or selected RNA pools. Moreover, it has been discovered that the half-life of a 2'-fluoro-modified RNA in human plasma is dependent upon the concentration of 2'-fluoro-modified pyrimidines present in the RNA, it is now possible to prepare 2'-fluoro-modified RNAs having defined, pharmodynamically preferred half-lives by simply controlling the ratio of 2'-fluoro-modified versus unmodified pyrimidine triphosphates within the RNA. It has also been discovered that incorporation of 2'-amino-2'-deoxycytidine and 2'-amino-2'-deoxyuridine into RNA also serves to increase the stability of the RNA stability at least one hundred-fold compared with unsubstituted RNA.

Example 10. Testing of the Modified Selected RNA Pool for Its Ability to Inhibit Virus Replication The selected pool was transcribed in the presence of 2'-fluoro-pyrimidines triphosphates in place of CTP and TP such that a 2'-fluoro-pyrimidine modified RNA pool of the selected sequences was obtained. RNAs so modified were tested for their ability to inhibit RSV replication (FIG. 8, lanes 1 and 2) and were found inhibit virus replication significantly in the assays described above. However, about seven to ten-fold more modified RNA was required to achieve levels of inhibition comparable to those achieved using unmodified RNAs.

It should be noted that in the above-described experiment, all the selections were performed using unmodified RNAS. The subsequently obtained RNA pool was modified by incorporation of nucleoside analogs at the last step. When the selection process is performed using modified RNAs, the amount of these RNAs required to effect inhibition of RSV replication is significantly lowered. For example, when the first nine selection cycles were performed using unmodified RNA and the RNA pool was subsequently converted to comprise 2'-fluoro-pyrimidine modified RNAs which were further selected for an additional three cycles, the resulting modified RNA pool was about 4.5 times more potent in inhibiting RSV than a modified RNA pool obtained by transcription of unmodified twelve times-selected nucleic acid templates. Thus, the introduction of modified nucleoside analogs into the RNA prior to completion of the selection process serves to enhance the antiviral activity of RNAs within the pool. It is therefore likely that an even more potent anti-RSV modified RNA pool may be obtained when all twelve selection cycles are performed using 2'-fluoro-pyrimidine modified RNAs.

Inhibition of virus replication was specific for modified RNAs contained within the selected pool in that modified RNAs obtained from the random pool had no effect on virus replication (FIG. 8C, lanes 3 and 4). In addition, modified RNA was not toxic to cells even at concentrations as high as 200 nM.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: unknown ( i i ) MOLECULE TYPE: RNA (genomic)

( x i ) SEQUENCE DESCRIPTION: SEQ ID NO:1:

GGGAGCUCAG AAUAAACGCU CAAGGGUAGG GAUCGUUACC CCGACAUUUU AAUGGGCCGA    60

UGUUUCGACA UGAGGCCCGG AUCCGGC    87

( 2 ) INFORMATION FOR SEQ ID NO:2:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: unknown ( i i ) MOLECULE TYPE: RNA (genomic)

( x i ) SEQUENCE DESCRIPTION: SEQ ID NO:2:

GGGAGCUCAG AAUAAACGCU CAAUGCCUCG UGUCGAAGAA GGGUGGCGCG AGGGUAGGGU    60

UUCGACAUGA UUCGACAUGA GGCCCGGAUC CGGC    94

( 2 ) INFORMATION FOR SEQ ID NO:3:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: unknown ( i i ) MOLECULE TYPE: RNA (genomic)

( x i ) SEQUENCE DESCRIPTION: SEQ ID NO:3:

GGGAGCUCAG AAUAAACGCU CAAUGUAGUG AACAUUAAUG GAGAGAGGGA GGGUAGGGUU    60

ACGUUCGACA UGAGGCCCGG AUCCGGC    87

( 2 ) INFORMATION FOR SEQ ID NO:4:

( i ) SEQUENCE CHARACTERISTICS:
        ( A ) LENGTH: 89 base pairs
        ( B ) TYPE: nucleic acid
        ( C ) STRANDEDNESS: single -continued

```
        ( D ) TOPOLOGY: unknown ( i i ) MOLECULE TYPE: RNA (genomic)

( x i ) SEQUENCE DESCRIPTION: SEQ ID NO:4:

G G G A G C U C A G   A A U A A A C G C U   C A A A U U G U C U   U G A A C C C G U G   G G A G G U G U G A   G G G U A G G G G U         6 0

G G U U C U U C G A   C A U G A G G C C C   G G A U C C G G C                                                                                 8 9

( 2 ) INFORMATION FOR SEQ ID NO:5:

( i ) SEQUENCE CHARACTERISTICS:
            ( A ) LENGTH: 88 base pairs
            ( B ) TYPE: nucleic acid
            ( C ) STRANDEDNESS: single
            ( D ) TOPOLOGY: unknown ( i i ) MOLECULE TYPE: RNA (genomic)

( x i ) SEQUENCE DESCRIPTION: SEQ ID NO:5:

G G G A G C U C A G   A A U A A A C G C U   C A A U A A U G U U   G G A C C U A G U G   G A G G G U G U G U   G G A G G G A U U G         6 0

G U U C U U C G A C   A U G A G G C C C G   G A U C C G G C                                                                                   8 8

( 2 ) INFORMATION FOR SEQ ID NO:6:

( i ) SEQUENCE CHARACTERISTICS:
            ( A ) LENGTH: 87 base pairs
            ( B ) TYPE: nucleic acid
            ( C ) STRANDEDNESS: single
            ( D ) TOPOLOGY: unknown ( i i ) MOLECULE TYPE: RNA (genomic)

( x i ) SEQUENCE DESCRIPTION: SEQ ID NO:6:

G G G A G C U C A G   A A U A A A C G C U   C A A U G U U A G G   A C C C U C G A G G   G A G G U U G C G C   A G G G U G G G A         6 0

G G G U U C G A C A   U G A G G C C C G G   A U C C G G C                                                                                     8 7

( 2 ) INFORMATION FOR SEQ ID NO:7:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: unknown ( i i ) MOLECULE TYPE: RNA (genomic)

( x i ) SEQUENCE DESCRIPTION: SEQ ID NO:7:

A U G U U A G G A C   C C U C G A G G G A   G G U U G C                                                                                       2 6
```

What is claimed is:

1. A method of identifying a compound which inhibits infection by infectious agents in vitro comprising the steps of A) incubating a library of single stranded nucleic acids or nucleic acid analogs in The presence of at least one population of intact infectious agents to effect binding of nucleic acid or nucleic acid analog in said library to said infectious agent, wherein said infectious agent is selected from the group consisting of virus, bacterium, fungus including yeast, and parasite;

B) separating infectious agent-bound nucleic acid or nucleic acid analog from unbound nucleic acid or nucleic acid analog to obtain a first pool of infectious agent-binding nucleic acid or nucleic acid analog;

C) amplifying said first infectious agent-binding nucleic acid or nucleic acid analog;

D) incubating said amplified first infectious agent-binding nucleic acid or nucleic acid analog in the presence of at least one population of intact infectious agents to effect binding of said nucleic acid or nucleic acid analog to said infectious agent;

E) separating amplified infectious agent-bound nucleic acid or nucleic acid analog from amplified unbound nucleic acid or nucleic acid analog to obtain a second infectious agent-binding nucleic acid or nucleic acid analog;

F) repeating said amplification step C, said incubation step D and said separation step E from zero up to about thirty times sequentially on each subsequently obtained infectious agent-binding nucleic acid or nucleic acid analog or repeating said steps C through E sufficient times to generate a pool of nucleic acids or nucleic acid analogs which bind to said infectious agent with high affinity; and G) assaying said subsequently obtained infectious agent-binding nucleic acid or nucleic acid analog for the ability to inhibit infection by said infectious agents in vitro.

2. The method of claim 1, wherein said nucleic acid or nucleic acid analog is single stranded RNA or RNA analog.

3. The method of claim 1, wherein said nucleic acid or nucleic acid analog is single stranded DNA or DNA analog.

4. The method of claim 1, wherein said single stranded nucleic acid or nucleic acid analog comprises from about 40 to about 450 nucleotide units.

5. The method of claim 1, wherein a core set of nucleotides within said nucleic acid or nucleic acid analog comprises a random or partially random nucleotide sequence.

6. The method of claim 5, wherein said core set of nucleotides comprises from about 10 to 350 nucleotide units.

7. The method of claim 1, wherein said amplification, incubation and separation steps performed sequentially on each subsequently obtained infectious agent-binding nucleic acid or nucleic acid analog are performed at least two times.

8. The method of claim 7, wherein said amplification, incubation and separation steps performed sequentially on each subsequently obtained infectious agent-binding nucleic acid or nucleic acid analog are performed at least four times.

9. The method of claim 8, wherein said incubation and amplification steps performed sequentially on each subsequently obtained infectious agent-binding nucleic acid or nucleic acid analog are performed at least twelve times.

10. The method of claim 1, wherein said population of infectious agents comprises at least one species of virus.

11. The method of claim 10, wherein said population of infectious agents comprises at least one strain of said species of virus.

12. The method of claim 10, wherein said species of virus is selected from the group consisting of human immunodeficiency virus, hepatitis virus A, hepatitis virus B, hepatitis virus C, hepatitis virus D, hepatitis virus E, herpes simplex virus type 1, herpes simplex virus type 2, varicella zoster virus, Epstein Barr virus, cytomegalovirus, human herpesvirus type 6, human herpesvirus type 7, human papilloma virus, human T cell leukemia virus and *Rous sarcoma* virus.

13. The method of claim 12, wherein said virus is human immunodeficiency virus.

14. The method of claim 12, wherein said virus is herpes simplex virus type 1 or herpes simplex virus type 2.

15. The method of claim 12, wherein said virus is human T cell leukemia virus.

16. The method of claim 12, wherein said virus is *Rous sarcoma* virus.

17. The method of claim 1, wherein said nucleic acid analog comprises substituted nucleotide units.

18. The method of claim 17, wherein said substituted nucleotide units confer resistance to nucleases and further wherein said substituted nucleotides are compatible with reverse transcription and polymerase chain reaction amplification.

19. The method of claim 18, wherein said substituted nucleotide units comprise substituted pyrimidines.

20. The method of claim 19, wherein said substituted pyrimidines comprise 2'-fluoro-pyrimidine.

21. The method of claim 20, wherein said 2'-fluoro-pyrimidine comprises: 2'-fluoro-2'deoxycytidine or 2'-fluoro-2'-deoxyuridine residues.

22. The method of claim 19, wherein said substituted pyrimidines comprise 2'-amino-pyrimidine.

23. The method of claim 2, wherein said 2'-amino-pyrimidine comprise 2'-amino-2'-deoxycytidine or 2'-amino-2'-deoxyuridine residues.

24. The method of claim 18, wherein said substituted nucleotide units comprise substituted purines.

25. The method of claim 24, wherein said substituted purines comprise 2'-fluoro-purine.

26. The method of claim 25, wherein said 2'-fluoro-purine comprises 2'-fluoro-2'-deoxyadenine or 2'-fluoro-2'deoxyguanidine residues.

27. The method of claim 24, wherein said substituted purines comprise 2'-amino-purine.

28. The method of claim 27, wherein said 2'-amino-purine comprises 2'-amino-2'deoxyadenine or 2'-amino-2'-deoxyguanidine residues.

29. The method of claim 1, wherein said assaying step is performed using an assay selected from the group consisting of a cell culture assay, an enzyme assay, an immunofluorescence assay, a nucleic acid assay and a protein assay.

30. A method of identifying a compound which inhibits viral infection in vitro comprising the steps of A) incubating a library of RNA and RNA analog molecules in the presence of at least one population of intact viruses to effect binding of said RNA or RNA analog to said viruses;

B) separating virus-bound RNA or RNA analog from unbound RNA or RNA analog to obtain a first virus-binding RNA or RNA analog;

C) amplifying said first virus-binding RNA or RNA analog;

D) incubating said amplified first virus-binding RNA or RNA analog in the presence of at least one population of intact viruses to effect binding of said RNA or RNA analog to said viruses;

E) separating amplified virus-bound RNA or RNA analog from amplified unbound RNA or RNA analog to obtain a second virus-binding RNA or RNA analog;

F) repeating said amplification step C, said incubation step D and said separation step E from zero up to about thirty times sequentially on each subsequently obtained virus-binding RNA or RNA analog; and G) assaying said subsequently obtained virus binding RNA or RNA analog for the ability to bind to said virus an inhibit replication of said virus in vitro.

31. A method of preparing a compound which inhibits viral infection in vitro comprising the steps of A) incubating a library of RNA or RNA flog molecules in the presence of at least one population of intact viruses to effect binding of said RNA or RNA analog to said viruses;

B) separating virus-bound RNA or RNA analog from unbound RNA or RNA analog to obtain a first virus-bound RNA or RNA analog;

C) amplifying said first virus-bound RNA or RNA analog;

D) incubating said amplified first virus-binding RNA or RNA analog in the presence of at least one population of intact viruses to effect binding of said RNA or RNA analog to said viruses;

E) separating amplified virus-bound RNA or RNA analog from amplified unbound RNA or RNA analog to obtain a second virus-binding RNA;

F) repeating said amplification step C, said incubation step D and said separation step E from zero up to about thirty times sequentially or repeating said steps C through E sufficient times to generate a pool of nucleic acids or nucleic acid analogs which bind to said infectious agent with high affinity;

G) assaying said amplified subsequently obtained virus-binding RNA or RNA analog for the ability to bind to said virus and to inhibit replication of said virus in vitro; and H) isolating and characterizing said subsequently obtained virus-binding RNA or RNA.

32. A compound generated by the method of claim 31.

33. The compound of claim 32, wherein said compound comprises RNA selected from the group consisting of Sequence B, E, F, G and H (SEQ ID NOS: 2, 3, 4, 5, and 6). analog.

34. An antiRSV composition comprising RNA selected from the group consisting of Sequence B, E, F, G and H (SEQ ID NOS: 2, 3, 4, 5 and 6).

* * * * *